(12) United States Patent
Kopanic, Jr. et al.

(10) Patent No.: US 7,300,409 B2
(45) Date of Patent: Nov. 27, 2007

(54) THERAPY PATCH

(75) Inventors: Robert J. Kopanic, Jr., Racine, WI (US); Pamela J. Taylor, Racine, WI (US); Daniel G. Lee, Milwaukee, WI (US); Jaime R. Allen, Milwaukee, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 11/252,033

(22) Filed: Oct. 17, 2005

(65) Prior Publication Data

US 2006/0258963 A1     Nov. 16, 2006

Related U.S. Application Data

(63) Continuation-in-part of application No. 11/127,493, filed on May 12, 2005, now Pat. No. 7,182,739.

(51) Int. Cl.
*A61H 1/00* (2006.01)

(52) U.S. Cl. .............................. 601/15; 601/46; 601/59; 601/70

(58) Field of Classification Search ................. 601/15, 601/46, 59, 70, 72, 152; 607/59, 70, 72, 607/152; 604/20; 602/2
See application file for complete search history.

(56) References Cited

U.S. PATENT DOCUMENTS

| 1,955,918 | A | 4/1934 | Jung, Jr. |
| 2,027,555 | A | 1/1936 | Scholl |
| 3,734,097 | A | 5/1973 | Zaffaroni |
| 4,343,303 | A | 8/1982 | Williams |
| 4,398,545 | A | 8/1983 | Wilson |
| 4,592,358 | A | 6/1986 | Westplate |
| 4,619,654 | A | 10/1986 | Abplanalp |
| 4,787,888 | A | 11/1988 | Fox |
| 4,887,594 | A | 12/1989 | Siegel |
| 4,982,742 | A | 1/1991 | Claude |
| 5,085,217 | A | 2/1992 | Shimizu |
| 5,415,866 | A | 5/1995 | Zook |
| 5,423,874 | A * | 6/1995 | D'Alerta .................... 607/72 |
| 5,902,256 | A | 5/1999 | Benaron |
| 6,155,995 | A | 12/2000 | Lin |
| 6,322,532 | B1 | 11/2001 | D'Sa et al. |
| 6,735,470 | B2 | 5/2004 | Henley et al. |
| 6,738,662 | B1 | 5/2004 | Frank |
| 6,908,448 | B2 | 6/2005 | Redding, Jr. |
| 2002/0156415 | A1 | 10/2002 | Redding, Jr. |
| 2004/0024348 | A1 | 2/2004 | Redding, Jr. |
| 2004/0236269 | A1* | 11/2004 | Marchitto et al. ............ 604/22 |
| 2005/0038377 | A1 | 2/2005 | Redding, Jr. |
| 2005/0049642 | A1 | 3/2005 | Bernabel |
| 2005/0059909 | A1 | 3/2005 | Burgess |
| 2005/0065461 | A1 | 3/2005 | Redding, Jr. |
| 2005/0085751 | A1* | 4/2005 | Daskal et al. ................. 602/2 |
| 2005/0234516 | A1* | 10/2005 | Gueret ......................... 607/3 |
| 2006/0015059 | A1 | 1/2006 | Redding, Jr. |

FOREIGN PATENT DOCUMENTS

| EP | 0278074 A2 | 8/1988 |
| FR | 1057283 | 3/1954 |
| WO | WO98/17184 | 4/1998 |

\* cited by examiner

*Primary Examiner*—Michael A. Brown

(57) ABSTRACT

Therapy patches provide portable massaging devices that can also deliver topical treatment chemicals. These patches can be adhered to the skin via an adhesive layer that is also impregnated with the treatment chemical. Kits are also provided to create a string of linked patches that can be used together or separately, and a microcontroller controls the vibration of the device for optimized massaging effects.

12 Claims, 2 Drawing Sheets

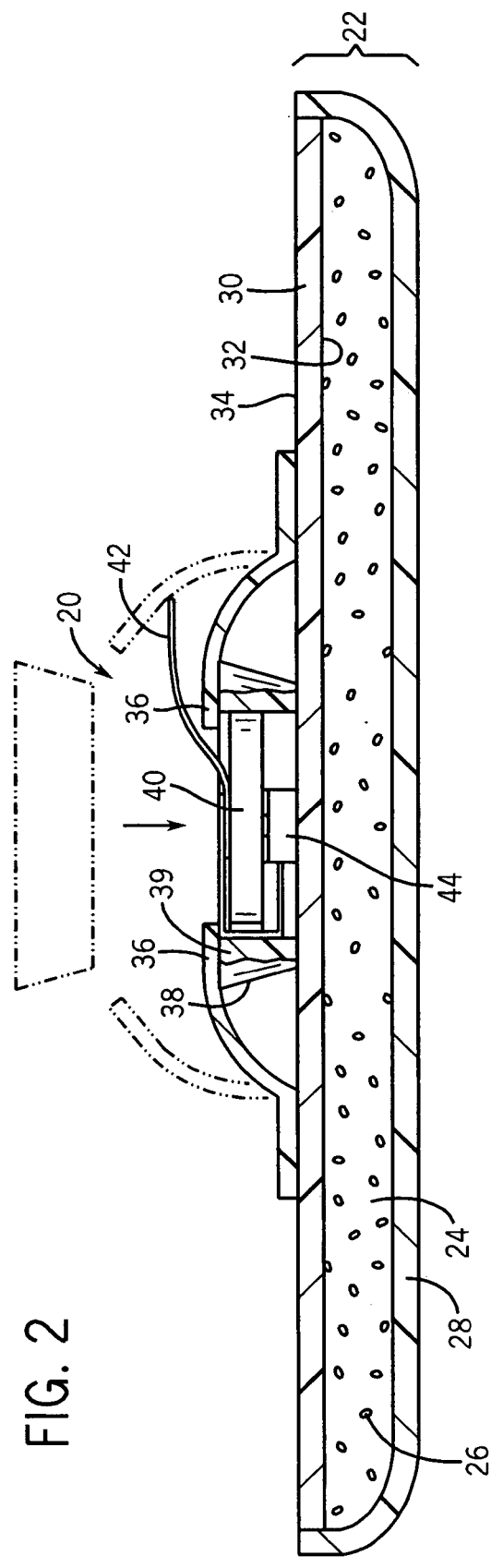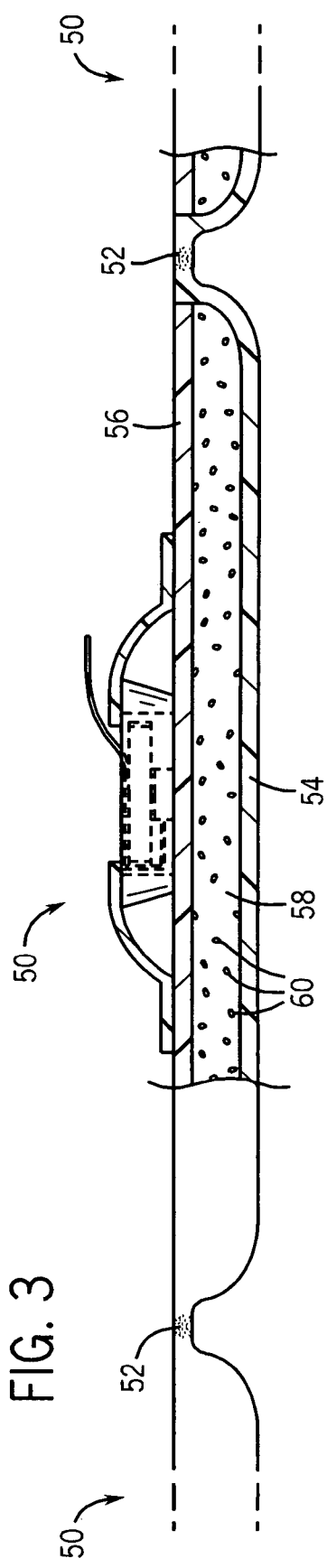
FIG. 2
FIG. 3

THERAPY PATCH

CROSS-REFERENCE TO RELATED APPLICATIONS

This application is a continuation-in-part application of U.S. application Ser. No. 11/127,493, filed on May 12, 2005 now Pat. No 7,182,739.

STATEMENT REGARDING FEDERALLY SPONSORED RESEARCH/DEVELOPMENT

Not applicable

BACKGROUND OF THE INVENTION

The present invention relates to therapy patches. It appears especially well suited to provide therapy patches configured to deliver a treatment chemical, along with vibration, to desired external areas of a human body. "Therapy" refers treatments to relax or otherwise provide beneficial sensation(s), such as for example to treat sore muscles.

Muscle pain can often be effectively treated by having a professional masseur massage the affected area. Such massages are sometimes supplemented with electrically powered hand-held massaging devices, and/or with chemicals (e.g. lotions) that are topically applied to the human skin during the massage. However, the services of a professional masseur can be expensive, require scheduling in advance, and typically require the person being massaged to be essentially immobile during the massage.

A number of devices have been developed that provide massaging effects without requiring a masseur. Many require an electrical power cord during operation, albeit some do not (e.g. U.S. Pat. No. 5,902,256).

A variety of patches have been developed for delivering treatment chemicals to a human (e.g. transdermally or topically). See e.g. U.S. Pat. Nos. 2,027,555 and 3,734,097. There have been efforts to improve the migration of those chemicals from such devices into the bloodstream employing ultrasound or an electric field. See e.g. U.S. Pat. Nos. 6,735,470 and 6,738,662 and U.S. patent application publications 2002/0156415, 2004/0024348, 2005/0038377, and 2005/0065461.

However, these prior art transdermal patches did not address ways to provide perceptible massage effects. Further, they did not address how a massaging vibration could be developed in connection with such a portable patch using an assembly that was sufficiently lightweight to permit the use of an adhesive application system.

Hence, a need exists for therapy patches that can provide massaging effects as well as a therapeutic chemical.

BRIEF SUMMARY OF THE INVENTION

In one aspect the invention can provide a therapy patch suitable to deliver massaging vibration, as well as a treatment chemical, to a target location on an animal body. While the preferred animals are expected to be humans, the invention may also have applicability in the veterinary field for a wide variety of mammals. By "massaging vibration" we mean generating a force and motions with an amplitude and frequency that can be felt at the skin surface by the animal being treated and is sufficient enough to affect muscle tissue below the targeted area. This force need not be constant or fixed. Moreover, even with respect to just humans, there is no one optimum force that is suitable for all massage needs for all persons. Consequently, one preferred device is expected to be one that can operate over a range of frequencies and amplitudes to provide the user with this range of forces and motions.

One therapy patch of the present invention could have a pad impregnated with the treatment chemical, a motor so associated with the pad so as to be able to cause the pad to vibrate in massaging fashion when the motor is operating, and means for attaching a battery to the motor. The battery and motor may be attached by a wide variety of means ranging from clips, covers, other mechanical attachments, and/or adhesives.

Most preferably the pad has an adhesive layer that is impregnated with the treatment chemical. That layer is designed to directly contact the human skin. A peel-off layer covers the adhesive layer prior to use. This facilitates shipment, handling and storage. It also prevents the treatment chemical from evaporating prior to use. Also helping inhibit premature dispersal of the impregnating chemical is a substrate layer that is impregnable with respect to the treatment layer and is positioned on an opposite side of the adhesive layer from the peel-off layer.

After the peel-off layer has been removed from the adhesive layer, the patch can be applied to a target location (e.g. the back of a human's neck) by having the adhesive layer directly adhere to the target location, and the motor can be initiated to provide a massaging vibration, the treatment chemical migrates from the adhesive layer to the target location, the animal can perceive the massaging effect, and the treatment chemical can be delivered to the skin. When the treatment chemical is one that generates a skin sensation of heat, the effect can be that of heat sensation combined with massage.

The power source for the motor can be a very lightweight battery. As the assembly does not require a power cord, the consumer remains free to move while receiving the massage. This battery is attached to the motor, preferably in a sub-assembly. The sub-assembly can be held against the pad by at least one flexible arm, or held in a recess in an upper surface of the pad, or otherwise linked to the pad. When the motor is in such a recess there can also be a removable cover such that the cover and recess form an enclosure for retaining and preferably hiding the sub-assembly.

In another preferred form there can be a controller capable of automatically causing the motor to repetitively turn on and off, to change motor speed, or both. This enhances the massaging effect.

The treatment chemical is preferably selected from a wide variety of chemicals that provide beneficial sensations, regardless of whether also providing medicinal effects. The most preferred treatment chemicals are expected to be those effective in addressing muscle aches or pains, such as analgesics, counter-irritants, pain relievers, numbing agents, corticosteroids, and combinations of these treatment chemicals. The patch may also provide one or more additional effects selected from the group consisting of sound, scent, and heat, and the patch may be linked to another such patch so as to be capable of being positioned with that other such patch along a target location.

The motor can be activated by removing a blocking tab, or by activating a depressible on/off switch, or by other known electrical control means.

In another aspect the invention provides a kit configurable to deliver a treatment chemical, as well as massaging vibration, to a target location on an animal. The kit has a motor capable of causing massaging vibrations when the motor is operating, means for attaching a battery to the motor, a first such patch, and a second such patch. The first and second patches are preferably connected along a linking web, and the linking web is sealed such that even after the first and second patches are separated by tearing or otherwise cutting through the linking web, so tearing or otherwise cutting through the linking web can be achieved without exposing the adhesive layer to ambient air.

With such a kit there can be at least two such motors, one of said motors being mountable to the first patch, and another of said motors being mountable to the second patch. The two motors are independently operable by a controller. This permits the creation of patterned massaging effects.

In another aspect the invention provides a method for applying a treatment chemical, in addition to massaging vibration, to human skin. One obtains a patch of the above kind, attaches it to human skin so that the treatment chemical can migrate to the skin, and activates the motor so as to cause the human skin to receive massaging vibration.

While a computer controller preferably can repetitively activate and deactivate the motor to create a pulsing sensation at a single locus, the controller can instead (or in addition) alter the speed of the motor and thus the amount of vibration in a defined way (e.g. a slow "warm up" speed, followed by a vigorous fast primary speed, followed by a slower "cool down" speed).

One may activate the motor before or after the patched is attached to the animal skin. For humans the attaching step can involve sticking the patch onto a human's skin through the use of the adhesive layer adhering directly to the pad and the skin. After the massage is complete, the patch can be completely disposed of. Alternatively, the assembly can be designed so that one can remove the motor and battery from a first patch that is used up, and use the motor (and possibly also the battery) with another fresh patch. Thus, the motor and battery do not necessarily have to be thrown away before their useful life is exhausted. Because the motor can be essentially centrally located in some preferred embodiments, its vibration effects can be optimally spread out throughout the patch. Hence, the size of the patch can be relatively large for a given desired maximum weight.

As the overall patch is very lightweight, the patch can be affixed to the skin and left in place for an extended period without the need for a human to continue to hold the device in place, or the need for the use of adhesives that are so strong that removal of the patch would cause considerable pain. Moreover, the small sizes of the battery and motor permit peripheral portions of the patch to be able to bend in shape, following the contours of the human body. This is expected to improve chemical transfer characteristics as one can avoid gaps between the patch bottom surface and the skin near the periphery of the device. Further, because the motor (and an incompletely used battery) can be moved to the next patch once the first patch chemical is exhausted, the cost of using the device is kept low.

The foregoing and other advantages of the present invention will be apparent from the following description. In the description that follows reference is made to the accompanying drawings which form a part thereof, and in which there is shown by way of illustration, and not limitation, expected preferred embodiments of the invention. Such embodiments do not necessarily represent the full scope of the invention, and reference should therefore be made to the claims herein for interpreting the scope of the invention.

BRIEF DESCRIPTION OF THE DRAWINGS

FIG. 2 is a sectional view thereof taken along line 2-2 of FIG. 1;

FIG. 3 is a side elevational view, partially broken away, of a series of connected therapy patches, the series being suitable for use as part of a preferred kit of the present invention;

DETAILED DESCRIPTION OF THE PREFERRED EMBODIMENTS

Figure 1:
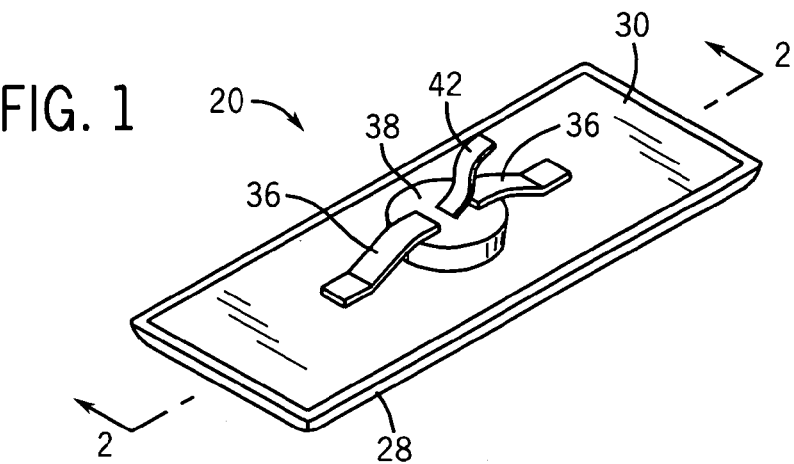
FIG. 1 is a frontal, top, right perspective view of a first preferred therapy patch of the present invention.

Referring first to FIGS. 1 and 2, a first therapy patch (generally 20) is disclosed. This patch is designed to deliver a treatment chemical as well as massaging vibration to human skin. Pad 22 has an adhesive layer 24 impregnated with a treatment chemical 26. The adhesive layer 24 is, until use, protected by a peel-off layer 28 on one side and backed by a support layer 30 on the other.

At least lower side 32 of the support layer 30 is preferably impermeable to the treatment chemical 26. Upper side 34 of the support layer 30 has a pair of spring arms 36 fixed thereon that can clamp a battery-motor sub-assembly 38 down in a removable fashion. The adhesive layer 24 is suitable to removably stick on human skin after peel-off layer 28 is removed. The treatment chemical 26 is then free to migrate from the adhesive layer 24 to the human skin.

While a wide variety of materials are suitable for the various layers of the pad, we prefer that the peel-off layer 28 be made of polypropylene. Of course, a wide variety of other materials (preferably plastics) can be used for this purpose. In this regard, the art is well developed with respect to peel-off layers used for traditional bandages and transdermal patches.

Similarly, the adhesive layer 24 be made of a wide variety of materials. In this regard, the adhesive layer can be a hydrogel material formed with carboxymethylcelluose sodium, glycerin, kaolin, methyl acrylate/2-ethylhexyl acrylate copolymer, polyacrylic acid, polysorbate 80, sodium polyacrylate, tartaric acid, titanium dioxide, and water. In another form, the hydrogel can be formed with acrylic acid, aluminum hydroxide, carmellose sodium, 2-ethylhexyl acrylate, glycerin, isopropyl myristate, methyl acrylate, nonoxynol-30, polyacrlyate, polyacrylic acid, polysorbate 80, sorbitan sesquioleate, starch, talc, tartaric acid, titanium dioxide, and water. In still another embodiment, the hydrogel can be formed with butylate hydroxytoluene, hydrogenated rosin glycerol ester, maleated rosin glycerin ester, natural rubber, perfume, polybutene, polyisobutylene, silicon dioxide, starch grafted acrylate, titanium dioxide, tocopherol acetate, and zinc oxide. We prefer that our adhesive layer be made of the hydrogel referred to above (formed with carboxymethylcelluose sodium, glycerin, kaolin, methyl acrylate/2-ethylhexyl acrylate copolymer, polyacrylic acid, polysorbate 80, sodium polyacrylate, tartaric acid, titanium dioxide, and water) when our treatment chemical is mentholatum.

Examples of other potential treatment chemicals include but are not limited to those that can stimulate, soothe, or otherwise affect skin sensation or treatment such as counter-irritants (e.g., menthol, methyl salicylate, mentholatum, camphor, peppermint oil extract, and capsaicin), analgesics (e.g., eucalyptus), numbing agents (e.g., lidocane and prilocain), and corticosteroids (e.g., alclometasone (Aclovate), clocortolone (Cloderm), desonide (DesOwen), and hydrocortisone (Cortizone-10 and Cortaid)). Some, like menthol, will be for topical effect. Others may be designed for entering the blood stream (e.g. certain analgesics).

We expect that a most preferred adhesive layer will be 2-3 mm thick, 600 cm$^2$ in area, and impregnated with 0.1 ml of the treatment chemical if mentholatum is used. We would propose to use therewith a polypropylene peel-off layer to cover one surface of it, which layer would be less than 1 mm thick.

The support layer 30 can be made of a wide variety of materials. For example, with the adhesive layer and peel-off layer of the prior paragraph we propose a support layer 30 made of polypropylene that is less than 1 mm thick.

The spring arms 36 can be made of plastics, metals, or other flexible materials. We prefer to use a plastic such as polypropylene.

The battery-motor sub-assembly 38 may have a resin casing 39, a battery 40, an initiator 42 and a motor 44, the latter having a vibrating attribute. In this regard, the motor 44 can have an internal off-center weight that rotates during operation (under self-contained battery power) to induce vibrations in the casing 39 (and thus the overall pad 22) that are communicated to the target skin when therapy patch 20 is attached to the skin surface.

Figure 5:
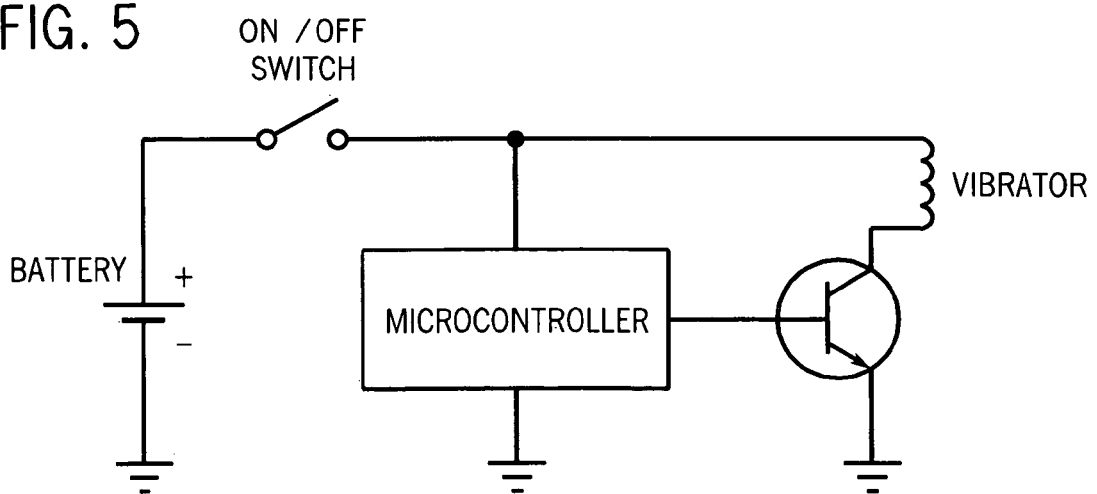
FIG. 5 is a circuit diagram showing possible control circuitry for an embodiment of the present invention.

The motor 44 and/or battery 40 can be designed for use with a first, and then one or more subsequent, therapy patches 20, or can be designed for use with only an original therapy patch, to be disposed of when the patch is thrown away. It is possible to control the motor 44 via a microcontroller linked to the sub-assembly to produce controlled pulsed on/off cycles. Microcontrollers capable of providing this feature are available from such companies as the Atmel Corporation. An example of possible circuitry to accomplish this is shown in FIG. 5.

To start motor operation, and as will be appreciated from FIG. 2, a pull tab initiator 42 can be removed, thereby permitting an upper contact of the motor 44 to bias down onto the battery 40. Alternatively the initiator 42 could be in the form of a switch that provides tactile feedback when depressed. When the motor is switched on, this will initiate vibration.

While the FIG. 2 embodiment of battery-motor sub-assembly has the battery on top of the motor, the battery-motor sub-assembly can also take a motor-on-top-of-battery form. With such a form, the upper surface of the motor can be exposed to a depression panel on the top of the puck, thereby permitting pressure to initiate the motor.

In FIG. 3 there is depicted a string of patches 50 that are linked together in tear-off fashion (e.g. analogous to a roll of kitchen paper towels). These patches 50 are rectangular in top view and each have a selected pad, motor, and battery arrangement of the sort described above (e.g., analogous to the FIG. 1 construction). A feature of particular interest with respect to FIG. 3 is that these patches are now linked together via web sections 52 and thus may provide a tear-off replacement supply. Alternatively, a series of linked patches can be used as a group, with multiple motors and batteries, to affect a more extended area on the body.

When linked patches are used as a group, with multiple motors and batteries, the motors may be allowed to run independently. Alternatively, they may be so governed as to operate in a coordinated way. As an example, if the motors in a connected series of patches are made to pulse in succession down the series, the effect could be a sensation of kneading, rolling, or pulsing motions across the body. A microcontroller (similar to that discussed above with respect to pulsing operation of a single patch) could be programmed to coordinate the activation of such a series of motors. Alternatively, most motors could be controlled to work continuously, while a particular motor (or motors) could be provided with special pulsing instructions. This might be a system suitable for focusing on a particular area of ache, while also more generally providing massaging and a treatment chemical.

When patches are to be used individually, one can, for example sever a patch 50 off of the string along the web section 52. Because the peel off layer 54 and the support layer 56 are sealed together in this region, the severing will not expose the adhesive layer 58 of the adjacent patch to air. Thus, this provides a unique replacement supply. When the chemical in a first patch 50 is exhausted, the motor and battery can be removed from that patch and positioned in the next patch that is torn off. However, the tearing process does not compromise the patches that are not to be immediately used.

Figure 4:
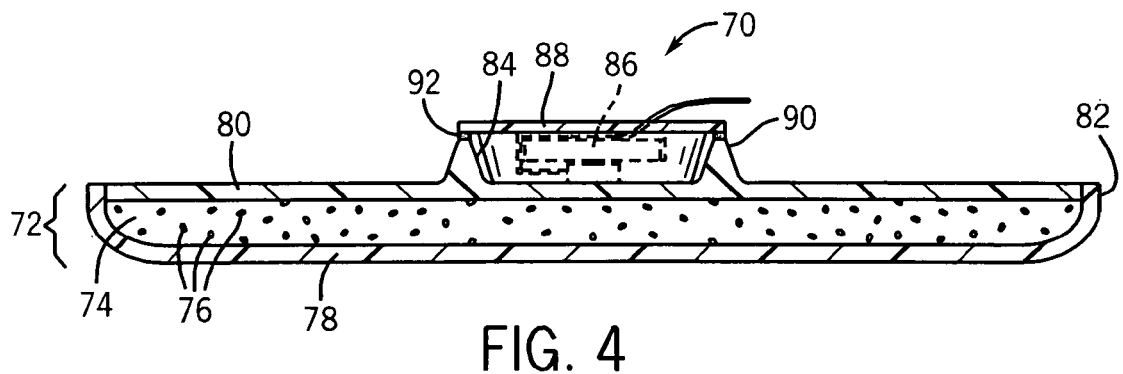
FIG. 4 is a sectional view of an alternative therapy patch of the present invention.

In FIG. 4 there is depicted another alternative patch 70. This construction is similar to that depicted in FIGS. 1 and 2 (e.g., it has an adhesive layer 74 impregnated with a treatment chemical 76, a peel off layer 78, and a support layer 80) except that pad 72 has a substantially annular periphery 82 and the support layer 80 defines a centrally disposed recess 84, rather than having spring arms attached for receiving battery-motor assembly 86. The recess 84 is sized to receive the battery-motor assembly 86.

Cover 88 is provided, which can be formed from a flocked PVC that spans over the battery-motor assembly 86, and is connected to wall 90 via an adhesive ring 92. The periphery of the recess 84 and the cover 88 cumulatively provide a casing that encapsulates the battery-motor assembly 86.

There are other possible alternatives for mounting the motor. Rather than having a permanent recess or a permanent set of tabs, one might construct the pad so that it automatically closes around the motor and battery once they are positioned in the pad, somewhat like a foldable coin purse.

The exact forms of the motor and battery are not critical, albeit it is highly preferred that they be extremely lightweight. Examples of a preferred motor and a preferred battery are the Sanko 1E120 motor from Sanko Electric Co., Ltd., of Taiwan, and the Energizer CR2430 battery from Energizer Holdings, Inc.

The therapy patch 20 could include additional features. For example, a suitable portion of the therapy patch 20 can be treated with a volatile scented material, for example such as lavender or peppermint oil, that is expected to be released into the air upon use of the patch. Sachets or other holders of volatile scented materials (not shown) similarly could be included on or within the therapy patch 20 for the same purpose. Furthermore, any suitable music or noise maker could be incorporated in the therapy patch 20, if the delivery of sound in conjunction with the other sensations provided by the patch is desired. Also, such a device could also deliver heat or cold temperatures to the surface being treated using techniques described in our priority application, which is incorporated by reference as if fully set forth herein.

While the patches of the present invention can be used at a variety of locations along human skin, it is expected to be most preferred to apply the patch along the back of the neck, or to the shoulder area.

In any event, the broad principles of the present invention can be applied in a wide variety of other ways apart from those specifically noted herein. Still other modifications may be made without departing from the spirit and scope of the invention. Thus, the claims (rather than just the preferred embodiments) should be reviewed in order to understand the full scope of the invention.

INDUSTRIAL APPLICABILITY

The present invention provides therapy patches that can topically deliver a treatment chemical with massaging vibration to human skin.

We claim:

1. A therapy patch suitable to deliver a massaging vibration, as well as a treatment chemical, to a target location on an animal, the therapy patch comprising:
   a pad impregnated with the treatment chemical;
   a motor so associated with the pad so as to be able to cause the pad to vibrate in massaging fashion when the motor is operating;
   a battery attached to the motor; and
   means for attaching a battery to the motor;
   wherein the battery and motor form a unitary sub-assembly, and that sub-assembly is removably held in a recess in an upper surface of the pad.

2. The therapy patch of claim 1, further comprising a removable cover, whereby the cover and recess form an enclosure for retaining the sub-assembly.

3. The therapy patch of claim 1, further comprising a controller capable of automatically causing the motor to repetitively turn on and off, to change motor speed, or both.

4. The therapy patch of claim 1 wherein the pad comprises an adhesive layer impregnated with the treatment chemical;
   wherein the adhesive layer is removably attached to a peel-off layer on one of its sides, and is linked to a substrate on another of its sides; and
   wherein the substrate is essentially impermeable to the treatment chemical.

5. The therapy patch of claim 1, wherein the treatment chemical is selected from the group consisting of analgesics, counter-irritants, pain relievers, numbing agents, corticosteroids, and combinations thereof.

6. The therapy patch of claim 5, wherein the treatment chemical is suitable for treatment of a muscle ache or a muscle pain in humans.

7. The therapy patch of claim 1, further comprising a tab that inhibits activation of the motor such that upon removal of the tab the motor is activated.

8. The therapy patch of claim 1, wherein the motor comprises a switch configured to be depressed to activate and deactivate the motor.

9. The therapy patch of claim 1, wherein the patch, when in use, also provides to the user one or more additional effects selected from the group consisting of sound, scent, and heat.

10. The therapy patch of claim 1, wherein the patch is linked to another such patch and is capable of being positioned with that other such patch along the target location.

11. A kit configurable to deliver a treatment chemical, as well as massaging vibration, to a target location on an animal, the kit comprising:
    a motor capable of causing massaging vibrations when the motor is operating;
    means for attaching a battery to the motor;
    a first patch; and
    a second patch;
    wherein both patches are impregnated with a treatment chemical;
    wherein the first and second patches are connected along a linking web, and the linking web is sealed such that even after the first and second patches are separated by tearing or otherwise cutting through the linking web, so tearing or otherwise cutting through the linking web can be achieved without exposing an adhesive layer of either patch to ambient air.

12. The kit of claim 11, wherein the first and second patches are linked together, there are at least two such motors, one of said motors is mountable to the first patch, another of said motors is mountable to the second patch, and the two motors are independently operable by a controller.

* * * * *